United States Patent [19]

DeLong et al.

[11] 4,173,975
[45] Nov. 13, 1979

[54] MAGNETIC MEANS FOR DETERMINING PARTIAL PRESSURE OF OXYGEN PARTICULARLY IN UNDERWATER BREATHING APPARATUS

[75] Inventors: Daniel L. DeLong, Stevensville; Edward L. Rich, III, Arnold, both of Md.

[73] Assignee: Westinghouse Electric Corp., Pittsburgh, Pa.

[21] Appl. No.: 875,654

[22] Filed: Feb. 6, 1978

[51] Int. Cl.² .................. A62B 7/00; G01R 33/12
[52] U.S. Cl. .................. 128/142 R; 73/27 A; 324/204
[58] Field of Search .......... 324/204; 73/23, 27 A; 310/330; 128/142 R, 142.2, 142.3, 142.4, DIG. 17

[56] References Cited

U.S. PATENT DOCUMENTS

| | | | |
|---|---|---|---|
| 1,899,503 | 2/1933 | Hansell | 310/330 |
| 2,416,344 | 2/1947 | Pauling | 324/204 |
| 2,467,211 | 4/1949 | Hornfeck | 324/204 |
| 2,476,304 | 7/1949 | Kells et al. | 324/204 |
| 2,689,332 | 9/1954 | Greene | 324/204 |
| 3,026,472 | 3/1962 | Greene et al. | 324/36 |
| 3,049,665 | 8/1962 | Hummel | 324/36 |
| 3,064,465 | 11/1962 | Richardson | 73/27 A |
| 3,539,913 | 10/1970 | Prival | 324/36 |
| 3,646,431 | 2/1972 | Janssen | 324/36 |
| 3,720,870 | 3/1973 | Sueda | 324/204 |
| 3,742,344 | 6/1973 | Hummel | 324/36 |
| 3,855,529 | 12/1974 | Langweiler | 324/251 |
| 4,056,098 | 11/1977 | Michel et al. | 128/142 R |

*Primary Examiner*—Robert J. Corcoran
*Attorney, Agent, or Firm*—D. Schron

[57] ABSTRACT

A paramagnetic oxygen sensor wherein a reference chamber is oscillated into and out of an air gap of a magnetic circuit by means of a piezoelectric bender bar. The oscillating reference periodically displaces the ambient gas under measurement in the air gap and causes a varying flux in the magnetic circuit which is sensed, amplified and provided as an output signal indicative of the partial pressure of oxygen of the gas mixture.

3 Claims, 16 Drawing Figures

MAGNETIC MEANS FOR DETERMINING PARTIAL PRESSURE OF OXYGEN PARTICULARLY IN UNDERWATER BREATHING APPARATUS

BACKGROUND OF THE INVENTION

1. Field of the Invention

The invention in general relates to oxygen sensors, and more particularly to a partial pressure of oxygen sensor using the paramagnetic properties of oxygen.

2. Description of the Prior Art

In the field of gas analysis and in various oxygen utilizing systems, it is often desired to know the amount of oxygen which is present. For some systems, the amount of oxygen is an indication of system efficiency and for other systems, such as in diving systems, the amount of oxygen in the gas mixture, particularly the partial pressure of oxygen, is critical for the sustaining of life.

One type of sensor utilized extensively in the diving field is the polarographic cell, a chemical cell which is both small and relatively rugged. Such cells, however, do have a limited shelf life as well as a limited operating life.

Another type of oxygen sensor utilizes the fact that oxygen is highly paramagnetic, that is, the magnetic susceptibility of oxygen is substantially greater than that of most other gases and this characteristic is utilized to measure to a high degree of accuracy, the concentration of oxygen in a gas mixture.

A variety of types of paramagnetic gas analyzers operate on the principal of establishing a certain flux in a magnetic circuit having a plurality of air gaps. The magnetic reluctance of the gap is periodically varied by placing first a test sample and then a reference sample into the gap thereby producing a flux variation which is proportional to a particular constituent of the gas being measured, for example, oxygen.

In one type of sensor, a wheel containing alternate reference and test cells is rotated by means of a motor so that the cells pass between the gaps of the magnetic circuit while in another type of device, a toothed rotor is utilized with each tooth as it passes into a magnetic gap constituting a reference, while each space between the teeth represents a sample condition. In yet another instrument which utilizes a single air gap, a pump is utilized to alternately pump in a test gas and a reference gas into a chamber surrounding the magnetic gap.

These instruments which require multiple gaps and motor driven wheels do not lend themselves readily to a rough environmental life as would be experienced, for example, in the diving field where small size, portability, and ruggedness, as well as high accuracy, is demanded. Although a single air gap circuit would reduce the size of the overall device, the requirement for a pumping system complicates matters.

The present invention provides for a sensor which is relatively small and rugged and eliminates the requirements for rotating motors and consequently eliminates the need for bearings, rotary seals, and motor shielding devices.

SUMMARY OF THE INVENTION

The present invention determines the partial pressure of a paramagnetic gas, such as oxygen, in a gas mixture containing the oxygen and a background gas and includes a magnetic circuit which has a single air gap. The circuit includes a flux source and opposing pole pieces defining an air gap. The device includes a piezoelectric bender bar and a reference chamber having a magnetic susceptibility similar to the background gas and being arranged for oscillatory movement into and out of the gap by means of the bender bar. A drive circuit is provided for causing the bender bar to oscillate and a circuit means is arranged to measure the change in magnetic flux in the magnetic circuit due to the reference chamber oscillating into and out of the gap.

DESCRIPTION OF THE PREFERRED EMBODIMENT

Figure 1:
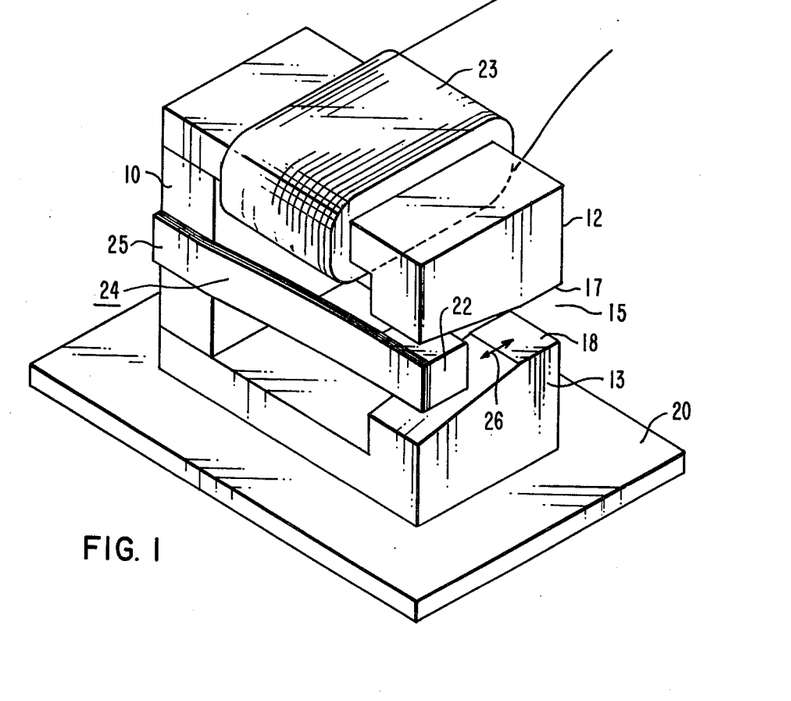
FIG. 1 is an isometric view of one embodiment of the present invention.

Referring now to FIG. 1, there is illustrated a magnetic circuit which includes a flux source such as a permanent magnet 10 and first and second pole pieces 12 and 13 defining an air gap 15. In order to increase the flux concentration per unit area, pole pieces 12 and 13 have reduced cross-sectional areas 17 and 18, respectively at the gap. If desired, pole piece 13 may be affixed to a base member 20 preferably of non-magnetic material.

In use, the circuit is immersed in an ambient gas mixture containing oxygen to be measured, and a background gas. This ambient gas fills the gap area resulting in a certain flux in the magnetic circuit. A reference chamber 22 having a magnetic susceptibility similar to the background gas is arranged for oscillatory movement into and out of the gap 15 and in the so doing will vary the magnetic flux with the variation being indicative of the presence of oxygen in the ambient gas, more particularly, the partial pressure of the oxygen. When the chamber is within the gap 15, it displaces the ambient gas therein and the magnetic field strength is that due to the background gas by virtue of the chamber 22 having the same susceptibility as the background gas. When the chamber moves out of the gap, the magnetic field strength is that determined by the oxygen of the gas mixture filling the gap.

In order to measure the change in magnetic flux in the magnetic circuit due to the reference chamber oscillating into and out of the gap 15, a flux change sensing means is provided and in one embodiment takes the form of a coil 23 wrapped around one (or more) of the pole pieces. The mechanism for oscillating the reference chamber 22 into and out of gap 15 is in the form of a piezoelectric bender bar arrangement 24 having one end, end 25, immovable relative to the gap 15 such as by adhesive attachment to permanent magnet 10. In a simplified embodiment, reference chamber 22 may be simply attached to the free end 26 of bender bar 24 so that when provided with a drive signal, the bender bar 24 will cause reference chamber 22 to oscillate into and out of gap 15 as indicated by the arrow 26.

Figures 2, 4:
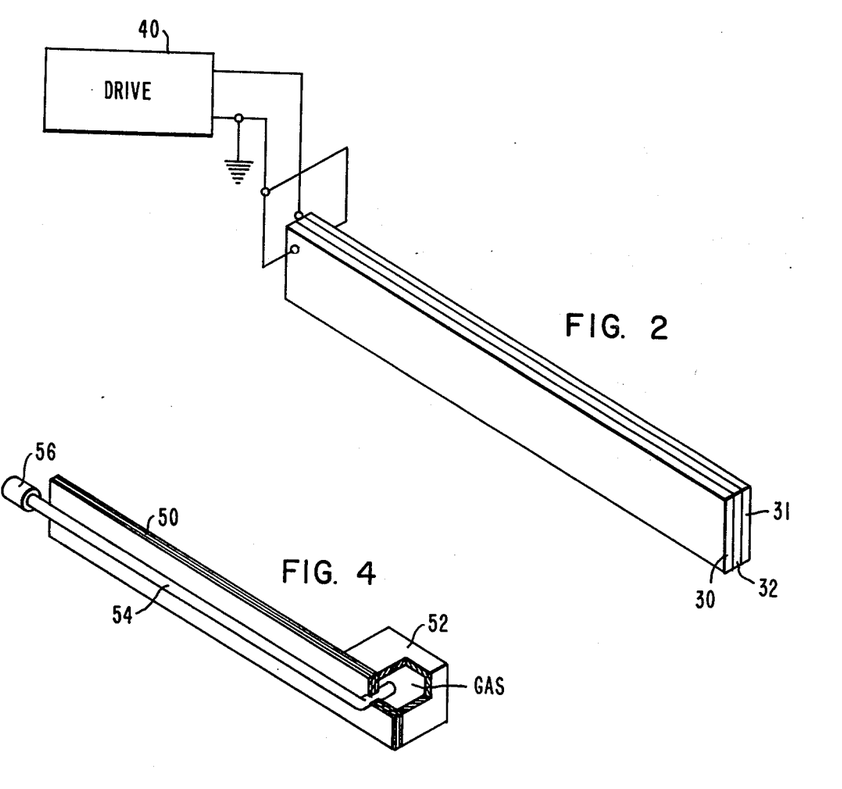
FIG. 2 is an isometric view of the bender bar shown in FIG. 1.
FIG. 4 is a view, with a portion broken away, of a bender bar in conjunction with a reference chamber, which may be pressure compensated.

Bender bars such as bender bar 24 are well known to those skilled in the art and are commercially available items. They generally comprise in one form or another a multiple layer structure of piezoelectric and metal. By way of example, FIG. 2 illustrates a three-layered structure made up of two piezoelectric layers 30 and 31, for example, lead-zirconate-titanate, with a layer of metal 32, for example brass, sandwiched between them.

Electrical leads are connected to the metal layer and to the electroded surfaces of the piezoelectric layers 30 and 31. The two outside leads are electrically connected together and they, along with the lead from the central metal layer 32, are provided with driving signals from drive source or circuit 40. Drive circuit 40 may provide either a sinusoidal or pulse-type signal and with the piezoelectric layers polarized such that when one layer expands or the other layer contracts upon the application of a signal, the required bending will occur. If the frequency of the drive source signal is equal to the natural frequency of oscillation of the bender bar with the reference chamber attached, the required driving power will be minimized.

Figure 3:
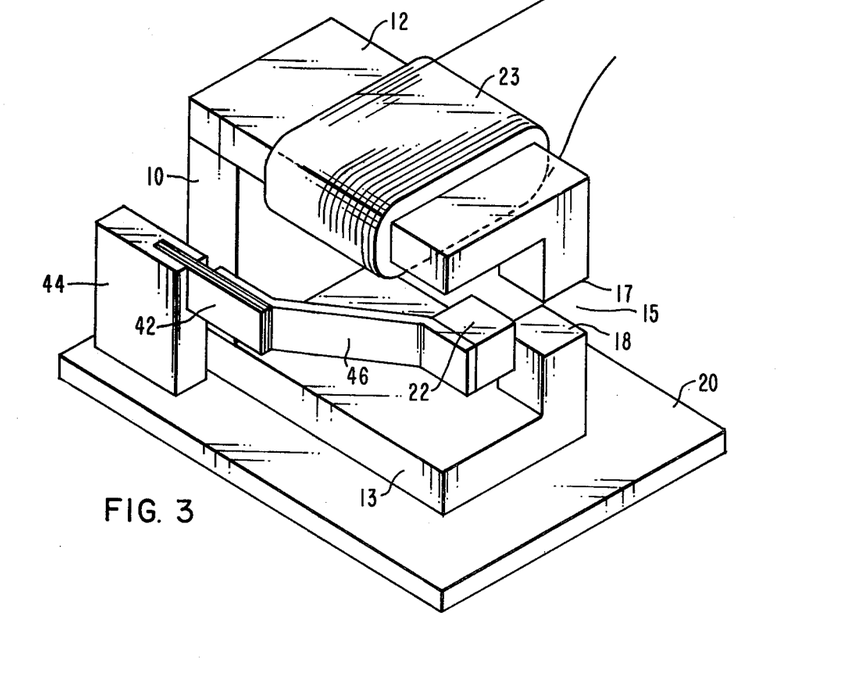
FIG. 3 is an isometric view of a variation of FIG. 1.

FIG. 3 illustrating several variations is similar to FIG. 1 and like components have been given the same reference numerals. Whereas in FIG. 1, the bender bar is attached to the permanent magnet, the arrangement of FIG. 3 illustrates the bender bar 42 being secured at one end thereof to an extension member 44 secured to the base member 20. In addition, bender bar 42 is much shorter and simply forms a short projection from the extension member 44. An extension arm 46 is connected to bender bar 42 and has, at the end thereof, the reference chamber 22 such that when suitable drive signals are provided to bender bar 42, reference chamber 22 will oscillate into and out of the gap 15, as was the case in FIG. 1.

Since the natural frequency of oscillation of the oscillatory unit is a function, inter alia, of the length and mass of the oscillating unit, the natural frequency thereof may be varied by varying the mass of the components making up the arm or by securing extension member 44 at other positions relative to the gap 15 with a commensurate increase or decrease in the length of the oscillating arm.

Various solid materials or mixtures thereof have a resultant susceptibility similar to the background gas in the gas mixture under measurement and accordingly, the reference chamber herein may be of such solid material. Alternatively, the reference chamber may be a hollow, thin-walled chamber into which is placed a gas mixture, with the combination having the same susceptibility as the background gas.

FIG. 4 illustrates such embodiment and includes a bender bar 50 having a hollow thin-walled reference chamber 52 secured to the end thereof with its interior filled with a gas. The gas may be introduced into the chamber during the fabrication process or alternatively, and as illustrated in FIG. 4, gas may be introduced into the chamber interior by means of a flexible tube 54 arranged along the length of bender bar 50 and having one end passing through bender bar 50 and reference chamber 52 with the other end connected to a gas fitting 56. This arrangement is particularly useful when the device is utilized in conjunction with diving equipment used at high pressures since the interior of reference chamber 52 may then be pressure compensated for the operating depth.

Figure 5:
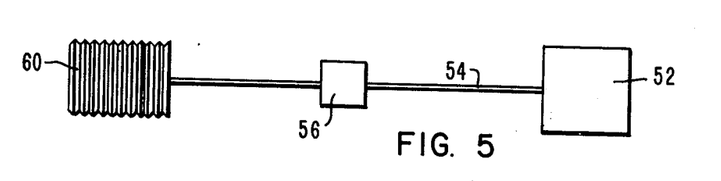
FIG. 5 is a schematic view of the pressure compensation of the reference chamber.

For example, and with reference to FIG. 5, gas fitting 56 may be connected to a bellows arrangement 60 subject to the ambient pressure which when exposed to increased pressures will compress to increase the gas pressure within the entire gas circuit, including reference chamber 52.

Figure 6:
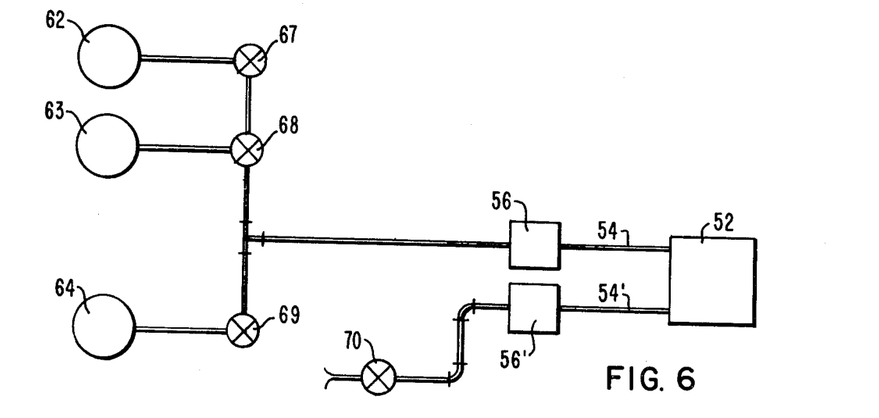
FIG. 6 is a schematic illustrating the provision of different reference gases to the reference chamber.

With the tubing and gas fittinbg arrangement, and as illustrated in FIG. 6, a plurality of gas supplies 62 through 64 may be provided with suitable valving arrangements 67 through 69 to allow reference chamber 52 to be filled with any one or a mixture of the gases. Previously used gas may be exhausted by means of tube 54', gas fitting 56' and valve 70.

Figure 7:
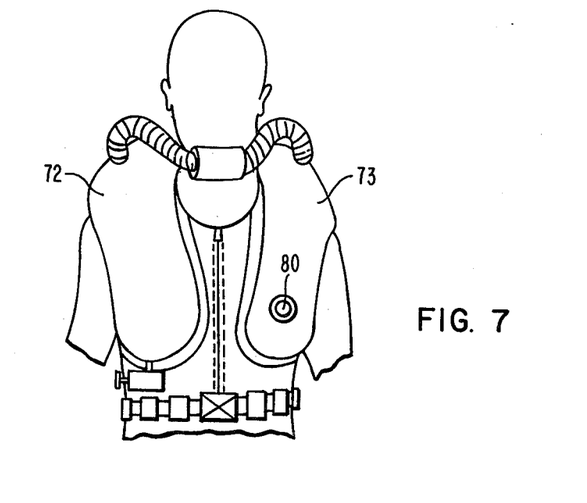
FIG. 7 is a view of a diver with diver worn breathing apparatus.

In various types of underwater breathing apparatus, the oxygen in the breathing circuit is constantly monitored by means of a sensor so that a proper amount of oxygen from a diver worn or remote supplied source may be added as necessary. The present invention is quite useful for such monitoring function. By way of example, FIG. 7 illustrates diver worn breathing apparatus including breathing bags 72 and 73. A monitoring unit 80 in accordance with the present invention is illustrated as being connected to one of the breathing bags, breathing bag 73. A portion of the breathing bag, together with a monitoring unit 80 with a portion broken away is illustrated in somewhat more detail in FIG. 8 to which reference is now made.

Figure 8:
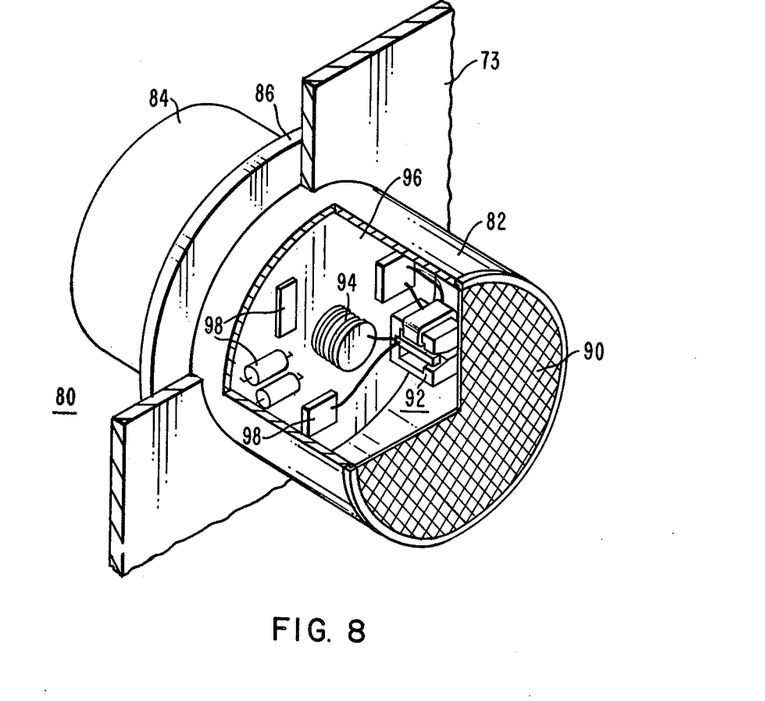
FIG. 8 is a view, with a portion broken away, of the oxygen sensing equipment of the present invention installed in a breathing bag of FIG. 7.

The monitoring apparatus is carried within cylindrical housing 82 inserted into container 84 having a flange 86 in gas-water sealing arrangement with breathing bag 73. Cylindrical housing 82 has a normally open end covered by a screen 90 in the interior of the breathing bag such that the ambient gas in the gas breathing circuit may enter housing 82. Positioned within housing 82 is a magnetic circuit and bender bar arrangement 92, such as described in FIG. 1. A bellows 94 provides pressure compensation as in FIG. 5 and the bellows may be mounted on a board 96 containing a plurality of electronic circuit components 98.

Figure 9:
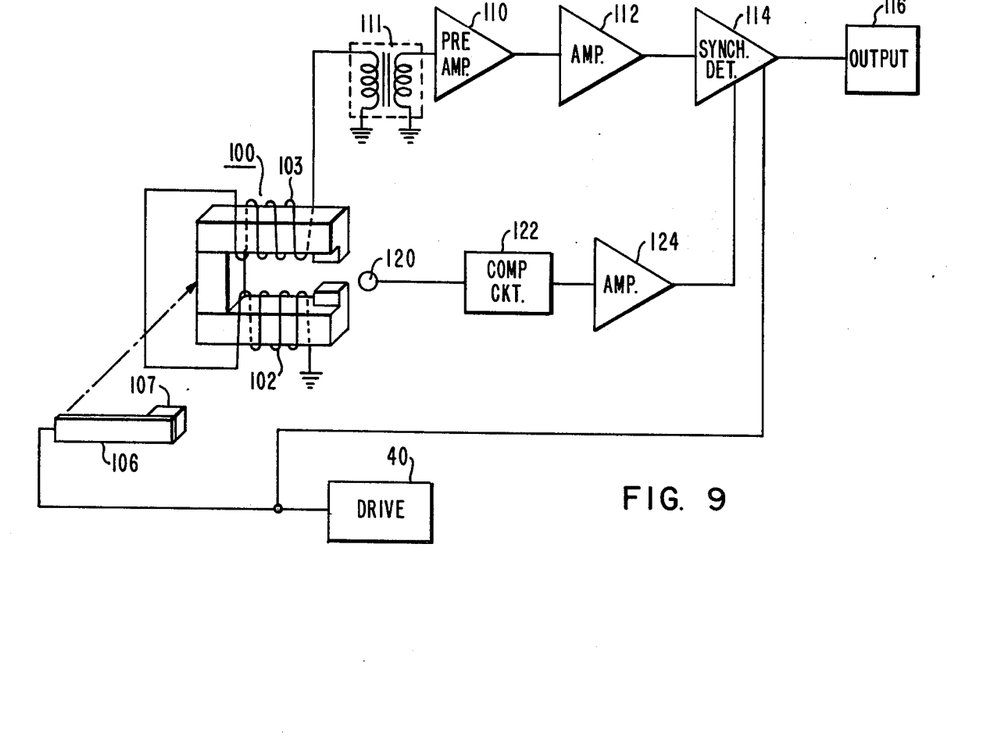
FIG. 9 illustrates an electrical block diagram for obtaining output readings.

FIG. 9 illustrates a circuit means for measuring the change in magnetic flux in the magnetic circuit to provide an output indicative of the oxygen in the gas under measurement. The circuitry of FIG. 9 may be used in any system wherein the oxygen is to be measured and with circuit components in integrated circuit form, the circuitry will fit into a small diver carried unit such as illustrated in FIG. 8.

The magnetic circuit 100 is similar to that illustrated in FIG. 1 except that two series arranged sense windings 102 and 103 are provided around respective pole pieces to sense the change in the flux. It will be understood that if desired, even more sense windings could be provided.

Bender unit 106 is arranged to move reference chamber 107 into and out of the air gap of the magnetic circuit under control of the drive unit 40 previously described with respect to FIG. 2.

Figure 10:
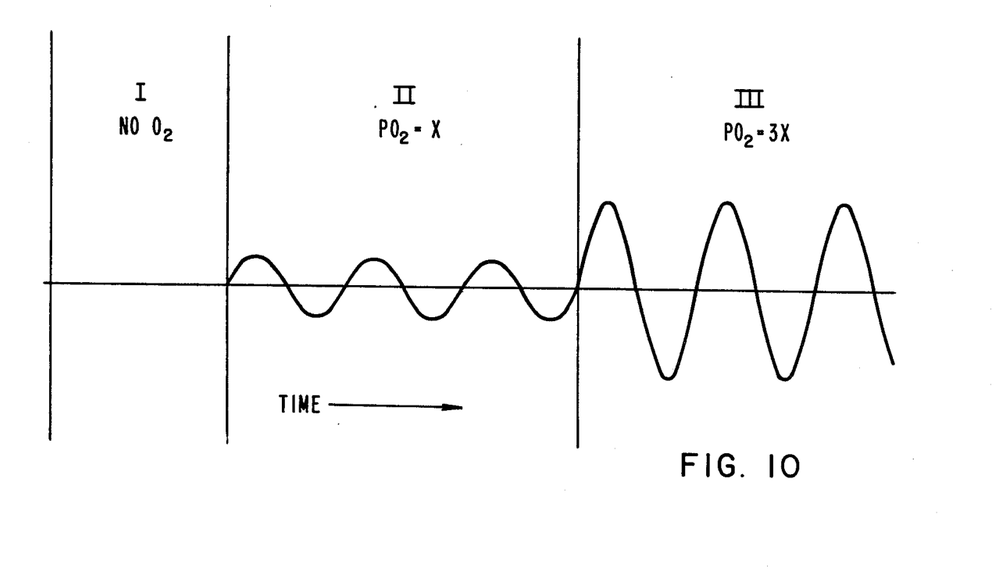
FIG. 10 illustrates the signal provided by apparatus such as illustrated in FIG. 1.

The output signal from the sense windings will vary in accordance with the oxygen concentration in the gas mixture under measurement. For example, FIG. 10 represents the sense winding output signal for three different oxygen conditions. In condition I, no oxygen is present and therefore, no output signal is provided. In condition II, a partial pressure of oxygen of a value X results in the signal illustrated, and in condition III, a partial pressure of oxygen of a value 3X results in a signal of a magnitude three times that of the signal in condition II.

Referring once again to FIG. 9, the sense winding output signal is provided to a preamplifier 110 by means of a shielded coupling transformer 111. Alternatively, although not shown, the transformer may have a balanced primary. Although other types of coupling are possible, the transformer coupling provides the added advantage of impedance matching the relatively low impedance of the sense windings to the relatively high impedance of the preamplifier, as well as providing some gain to the signal without noise from the input stage of the preamplifier.

Further amplification of the signal takes place in the amplifier 112, the output signal of which is provided to a synchronous detector circuit 14 additionally receiving the drive signal from drive circuit 40, resulting in a DC output signal, the level of which is proportional to the partial pressure of oxygen in the gas under measurement. The DC signal may be used for control or display purposes and is illustrated as being provided to an output circuit 116 which in one form may simply be a meter calibrated in partial pressure of oxygen units.

With the use of a permanent magnet as illustrated in FIG. 9, the flux in the magnetic circuit varies as the temperature varies. If large temperature variations are encountered in the ambient atmosphere where the apparatus is being used, an output signal may be provided which is due solely to temperature changes and not to oxygen content. Therefore, in order to better enhance the accuracy of the apparatus, means are provided for thermal compensation.

Included in the thermal compensation arrangement is a thermistor 120 positioned adjacent either the permanent magnet or one of the pole pieces to provide an output signal indicative of the temperature thereof. If the output of thermistor 120 is non-linear, a compensation circuit 122 may be provided in order to modify the voltage temperature characteristics such that a non-linear resistance change with temperature is converted into a linear voltage change with the temperature. The signal is amplified by means of amplifier 124, the output of which is a control signal which may be utilized to modify the gain of the flux signal being processed in the detector 114, for example.

The apparatus of the present invention is not limited to diving systems but may be used in a variety of environments wherein the oxygen content is required to be known. The apparatus may be positioned at various monitoring locations and left unattended and for various installations, the output 116 may take the form of telemetry equipment for transmitting oxygen readings to a central locations.

Figure 11A:
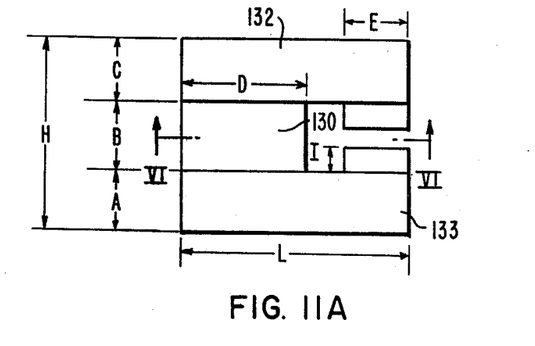
FIG. 11A is an elevation view, 11B a front view, and 11C a view along the line II—II of FIG. 11B of a typical magnetic circuit which may be utilized herein.
Figure 11B:
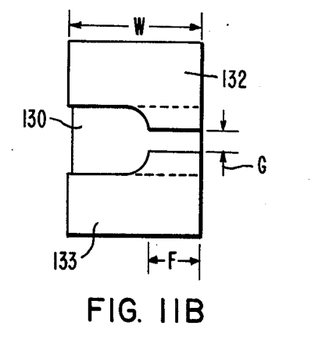
Figure 11C:
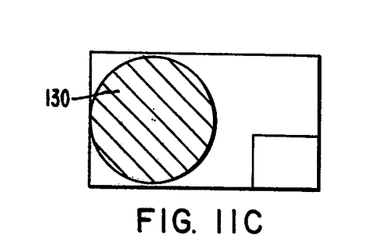

The magnetic circuit, bender bar and reference chamber may be fabricated and assembled in a variety of forms and FIGS 11A, B, and C illustrate, merely by way of example, one operative embodiment of the magnetic circuit. The flux source 130 is in the form of a permanent magnet, preferably a samarium cobalt magnet cylindrical in form and positioned between flux conducting pole pieces 132 and 133.

Typical dimensions indicated are as follows:

| | |
|---|---|
| A - 0.290 in. | (0.737 cm) |
| B - 0.220 in. | (0.559 cm) |
| C - 0.290 in. | (0.737 cm) |
| D - 0.450 in. | (1.143 cm) |
| E - 0.250 in. | (0.635 cm) |
| F - 0.150 in. | (0.381 cm) |
| G - 0.040 in. | (0.102 cm) |
| H - 0.800 in. | (2.032 cm) |
| I - 0.090 in. | (0.229 cm) |
| L - 0.850 in. | (2.159 cm) |
| W - 0.500 in. | (1.270 cm) |

Figure 12:
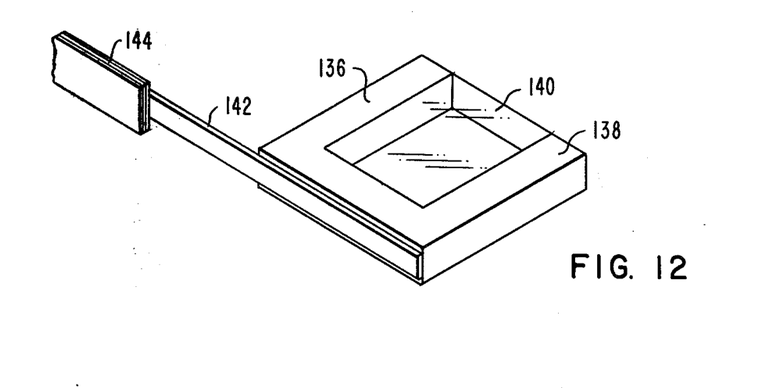
FIG. 12 is a view of one embodiment of a gas reference chamber which may be utilized herein.

Reference chamber 136 in FIG. 12 is formed from a lightweight C-shaped support member 138 over which is stretched and fastened a film 140 such as kapton, with the interior space between film 140 and support 138 being filled with a gas such that the susceptibility of the reference chamber walls and contained gas, within the gap of the magnetic circuit, have a combined volumetric susceptibility the same as the background gas. An extension arm 142 extends between, and is connected to, bender bar 144 and the support 138 of reference chamber 136, such extension arm being formed of a relatively stiff material, such as a glass capillary tube.

Figure 13:
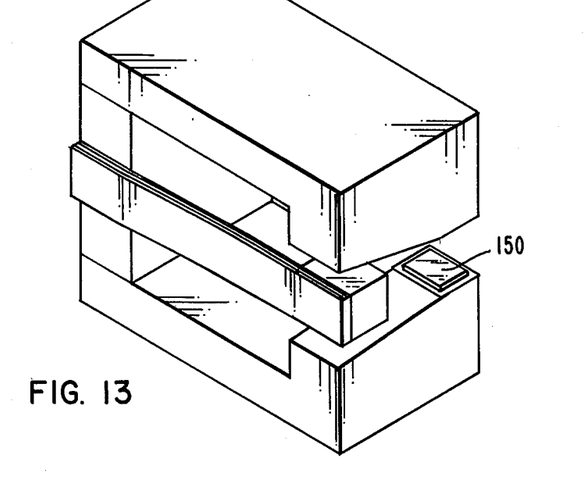
FIG. 13 is an isometric view of an alternate embodiment of the present invention.

The change in flux sensor has been described with respect to a coil or coils wound about the pole pieces of the magnetic circuit. FIG. 13 illustrates in an arrangement similar to FIG. 1, an alternative sensor in the form of a Hall effect device 150 positioned in the gap of the magnetic circuit.

Figure 14:
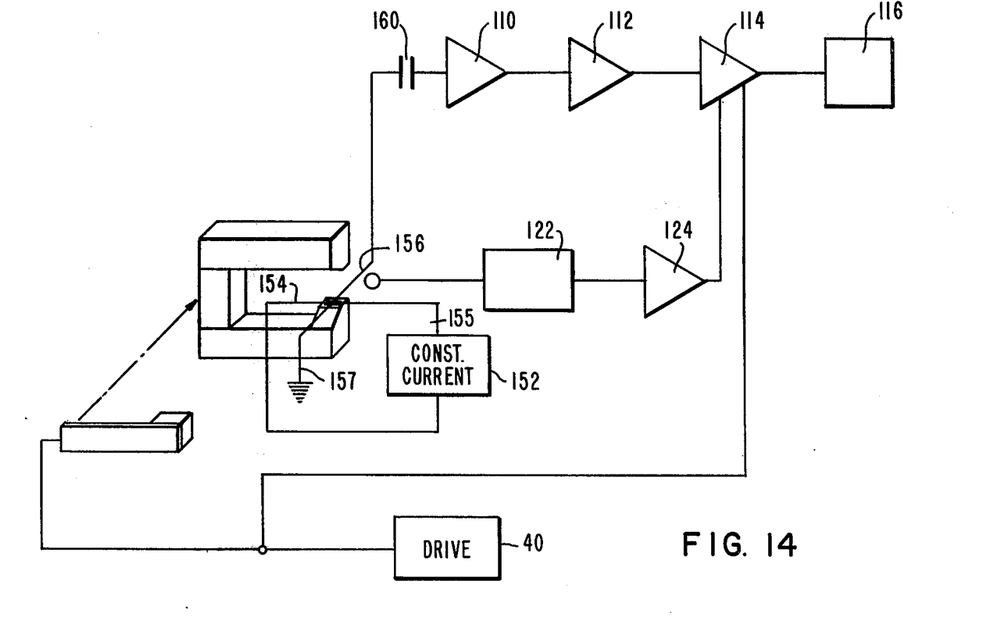
FIG. 14 illustrates an electrical block diagram for obtaining output readings from the apparatus of FIG. 13.

The Hall effect device is well known and as illustrated in the circuit of FIG. 14, a constant current generator 152 provides a constant current across the hall device through one pair of leads 154, 155. An output voltage across leads 156, 157 is then obtained which is proportional to the product of current times the magnetic field across the Hall device. The output signal from the Hall device may then, by means of capacitor 160, be coupled to the signal processing apparatus as previously described in FIG. 9.

What we claim is:

1. Apparatus for determining the partial pressure of oxygen in a gas mixture containing oxygen and a background gas comprising:
    (A) a magnetic circuit including a magnetic flux source and opposing pole pieces defining a gap;
    (B) a piezoelectric bender unit;
    (C) a reference chamber having a magnetic susceptibility similar to said background gas;
    (D) said reference chamber being arranged for oscillatory movement into and out of said gap by means of said bender unit;
    (E) drive means for oscillating said bender unit;
    (F) circuit means for measuring the change in magnetic flux in said magnetic circuit due to said reference chamber oscillating into and out of said gap to provide an output signal indicative of said oxygen;

(G) said reference chamber being hollow and containing a gas therein; and
(H) means for equalizing the pressure of said gas within said reference chamber with the pressure of said gas mixture.

2. Apparatus according to claim 1 which includes:
(A) underwater breathing apparatus having a breathing gas circuit for use by a diver;
(B) said magnetic circuit, bender unit, and reference chamber being positioned within said breathing gas circuit.

3. Apparatus according to claim 2 wherein:
(A) said breathing circuit includes at least a breathing bag;
(B) said magnetic circuit, bender unit, and reference chamber being positioned within said breathing bag.

* * * * *